United States Patent [19]

Deckelbaum et al.

[11] Patent Number: 5,350,375
[45] Date of Patent: Sep. 27, 1994

[54] METHODS FOR LASER INDUCED FLUORESCENCE INTENSITY FEEDBACK CONTROL DURING LASER ANGIOPLASTY

[75] Inventors: Lawrence I. Deckelbaum, Woodbridge; John J. Scott, Milford, both of Conn.

[73] Assignee: Yale University, New Haven, Conn.

[21] Appl. No.: 31,540

[22] Filed: Mar. 15, 1993

[51] Int. Cl.⁵ ............................................. A61B 17/36
[52] U.S. Cl. ......................................... 606/7; 606/15; 128/634; 128/898
[58] Field of Search ................. 606/7, 10–12, 606/3, 15; 128/633, 634, 898; 607/89

[56] References Cited

U.S. PATENT DOCUMENTS 4,718,417  1/1988  Kittrell et al.
4,785,806  11/1988 Deckelbaum.
5,106,387  4/1992  Kittrell et al. ............................ 606/7
5,115,137  5/1992  Andersson-Engels et al.

OTHER PUBLICATIONS

Deckelbaum et al., "In-Vivo Fluorescence Spectroscopy of Normal and Atherosclerotic Arteries", SPIE, vol. 906, Optical Fibers in Medicine III, 1988, pp. 313–319.

Primary Examiner—Stephen C. Pellegrino
Assistant Examiner—Michael Peffley
Attorney, Agent, or Firm—Wolf, Greenfield & Sacks

[57] ABSTRACT

Methods are provided for laser induced fluorescence intensity feedback and control during laser angioplasty. In a first aspect of the invention, a catheter including an eccentric guidewire lumen and at least one optical fiber is positioned relative to an obstruction in a blood vessel by rotating the catheter and monitoring the fluorescence intensity. When the fluorescence intensity has a maximum value, the optical fiber is aligned with the obstruction. In another aspect of the invention, fluorescence intensity feedback is used to determine when a laser ablation device has crossed an occlusion. An abrupt drop in fluorescence intensity indicates that the ablation device has crossed the occlusion. In a further aspect of the invention, fluorescence intensity feedback is used to determine the effectiveness of fluid flushing in a blood vessel. In yet another aspect of the invention, fluorescence spectroscopy and fluorescence intensity monitoring are performed sequentially for different subsets of optical fibers in a laser catheter to provide precise control over fiber positioning, tissue diagnosis and ablation. Preferably, the fluorescence intensity feedback is used in conjunction with fluorescence spectroscopy.

11 Claims, 5 Drawing Sheets

METHODS FOR LASER INDUCED FLUORESCENCE INTENSITY FEEDBACK CONTROL DURING LASER ANGIOPLASTY

FIELD OF THE INVENTION

This invention relates to improved techniques for laser angioplasty and, more particularly, to methods for laser catheter control using laser induced fluorescence intensity feedback.

BACKGROUND OF THE INVENTION

Removal of plaque deposits from blood vessels by laser ablation has been widely studied. Typically, a laser catheter is advanced through a blood vessel to a region that is partially or totally occluded by atherosclerotic tissue. One or more optical fibers extend through the catheter to its distal end. Laser energy sufficient to vaporize the atherosclerotic tissue is transmitted through the optical fibers to the obstruction.

One of the problems associated with laser ablation of atherosclerotic tissue is that of ensuring that the laser energy is directed at atherosclerotic tissue rather than normal arterial tissue. It is highly desirable to avoid damage to normal arterial tissue and, in particular, to avoid perforation of the vessel wall.

Laser induced fluorescence spectroscopy has been demonstrated as a technique for distinguishing between normal tissue and atherosclerotic tissue at the distal end of a laser catheter. Low level laser radiation, typically ultraviolet laser radiation, is transmitted in an antegrade direction through an optical fiber in the laser catheter to the occluded region and causes the tissue to fluoresce. The fluorescence is carried in a retrograde direction through the optical fiber to spectrum analysis equipment. By analyzing the fluorescence spectrum, normal tissue and atherosclerotic tissue can be distinguished. When atherosclerotic tissue is identified at the distal end of the laser catheter, high power laser energy is delivered, causing the atherosclerotic tissue to be ablated. Spectral analysis followed by ablation is repeated until atherosclerotic tissue is no longer indicated. This technique is described in U.S. Pat. No. 4,785,806 issued Nov. 22, 1988 to Deckelbaum. Techniques for laser induced fluorescence analysis are also disclosed in U.S. Pat. No. 4,718,417 issued Jan. 12, 1988 to Kittrell et al and U.S. Pat. No. 5,115,137 issued May 19, 1992 to Andersson-Engels et al.

It has been found that tissue fluorescence is strongly attenuated by blood, as described by L. I. Deckelbaum et al in "In-Vivo Fluorescence Spectroscopy of Normal and Atherosclerotic Arteries", SPIE, Vol. 906, Optical Fibers in Medicine III, 1988, pages 314–319, To avoid unacceptable attenuation of fluorescence, the distal end of the optical fiber can be positioned within about 100 micrometers of the tissue to be diagnosed. When laser angioplasty is performed in the presence of blood, it has been difficult to determine the position of the optical fiber tip relative to the tissue. Alternatively, a fluid, such as saline, that is transparent to the laser radiation can be introduced into the treatment region. When laser angioplasty is performed with saline flushing, it has been difficult to determine whether the flushing has effectively removed blood from the region of interest.

It is a general object of the present invention to provide improved methods for laser angioplasty.

It is another object of the present invention to provide methods for controlling the position of an eccentric laser catheter using laser induced fluorescence intensity feedback.

It is yet another object of the present invention to provide methods for determining, by laser induced fluorescence intensity feedback, when the distal end of a laser catheter has crossed an occlusion.

It is still another object of the present invention to provide methods for determining, by laser induced fluorescence intensity feedback, the effectiveness of fluid flushing in a blood vessel.

It is a further object of the present invention to provide a method for determining, by laser induced fluorescence intensity feedback, the position of subsets of optical fibers in a laser catheter relative to tissue.

SUMMARY OF THE INVENTION

According to the present invention, these and other objects and advantages are achieved in methods for laser induced fluorescence intensity feedback and control. In accordance with a first aspect of the invention, a method for positioning a catheter relative to tissue in a blood vessel comprises the steps of advancing a catheter, including an eccentric guidewire lumen and at least one optical fiber, through a blood vessel to a region of interest, stimulating fluorescence of tissue in the region of interest by transmitting through the optical fiber laser radiation having a wavelength and intensity to stimulate the fluorescence, monitoring the intensity of the fluorescence from tissue in the region of interest, and rotating the catheter in the blood vessel until the intensity of the fluorescence is representative of a desired position of the optical fiber relative to the tissue in the region of interest. Typically, the catheter is rotated until the fluorescence intensity exceeds a predetermined threshold value representative of tissue in contact with the distal end of the optical fiber.

According to another aspect of the invention, a method for ablating an occlusion in a blood vessel comprises the steps of advancing a catheter through a blood vessel to an occlusion, the catheter including an optical fiber extending therethrough, ablating tissue in the occlusion by transmitting laser radiation through the optical fiber, stimulating fluorescence from material in a region of the occlusion adjacent to the distal end of the optical fiber by transmitting through the optical fiber laser radiation having a wavelength and intensity to stimulate such fluorescence, monitoring the intensity of the fluorescence from material in the region of the occlusion, and continuing to ablate tissue in the occlusion until the intensity of the fluorescence is representative of blood, thereby indicating that the distal end of the catheter has crossed the occlusion. Typically, ablation of tissue in the occlusion is continue until the fluorescence intensity drops below a predetermined threshold value representative of blood adjacent to the distal end of the optical fiber.

According to a further aspect of the invention. a method for determining the effectiveness of fluid flushing in a blood vessel comprises the steps of advancing a catheter through a blood vessel to region of interest, the catheter including an optical fiber extending therethrough, introducing a flushing fluid into the region of interest in the blood vessel, stimulating fluorescence from material in the region of interest adjacent to the distal end of the optical fiber by transmitting through the optical fiber laser radiation having a wavelength and intensity to stimulate such fluorescence, monitoring the intensity of the fluorescence from material in the region of interest, and increasing the amount of flushing fluid in the region of interest if the intensity of the fluorescence is representative of less than a desired amount of flushing fluid in the region of interest. Typically, the amount of flushing fluid is increasing until the fluorescence intensity exceeds a predetermined value representative of the desired amount of flushing fluid in the region of interest.

According to still another aspect of the invention, a method for ablating atherosclerotic tissue in a blood vessel comprises the steps of (a) advancing a catheter through a blood vessel to a stenosed region, the catheter including two or more optical fibers, (b) stimulating fluorescence from tissue in the stenosed region by transmitting through a subset of the optical fibers laser radiation having a wavelength and intensity to stimulate such fluorescence, (c) analyzing the spectrum of the fluorescence transmitted through the subset of the optical fibers to distinguish between normal tissue and atherosclerotic tissue, (d) monitoring the intensity of the fluorescence transmitted through the subset of the optical fibers, (e) ablating tissue in the stenosed region by transmitting laser radiation through the subset of the optical fibers if the spectrum of the fluorescence is representative of atherosclerotic tissue and the intensity of the fluorescence is representative of a desired position of the subset of the optical fibers relative to the atherosclerotic tissue, and (f) repeating steps (b) through (e) for two or more different subsets of the optical fibers.

In each of the above methods, the sum of fluorescence intensities at two or more wavelengths can be monitored. In a preferred embodiment, the sum of fluorescence intensities at 380 nanometers and 440 nanometers is monitored. Alternatively, the fluorescence intensity can be monitored over a broad band or at a single wavelength, preferably 380 nanometers. The fluorescence is preferably stimulated by laser radiation in a wavelength of 280 to 400 nanometers.

BRIEF DESCRIPTION OF THE DRAWINGS

For a better understanding of the present invention, together with other and further objects, advantages and capabilities thereof, reference is made to the accompanying drawings, which are incorporated herein by reference and in which.

DETAILED DESCRIPTION OF THE INVENTION

Figure 1:
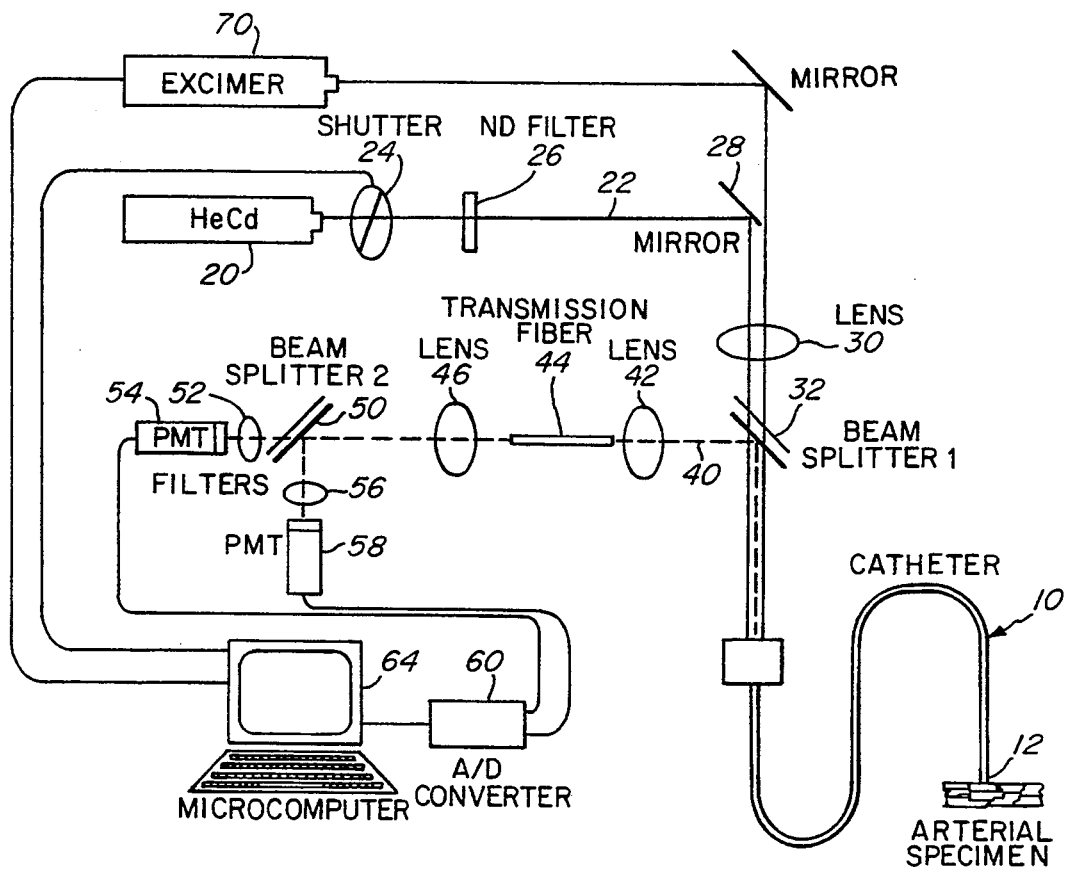
FIG. 1 is a block diagram of a fluorescence guided laser angioplasty system suitable for practice of the methods of the present invention.

A block diagram of a fluorescence guided laser angioplasty system, suitable for practice of the methods of the present invention, is shown in FIG. 1. A laser catheter 10 includes an elongated, flexible tube having at least one optical fiber extending therethrough to a distal end 12 and may include one or more lumens for a guidewire and for fluid flushing of the treatment region. The diameter and flexibility of the catheter are such that it can be advanced through a blood vessel to a stenosed region. Although the catheter 10 is shown in FIG. 1 as irradiating an arterial specimen in vitro, the catheter is typically used for removing obstructions in blood vessels. Various laser catheter structures are known to those skilled in the art.

A diagnostic laser 20 directs a low power laser beam 22 through a shutter 24 and a neutral density filter 26. The laser beam 22 is reflected by a mirror 28 through a lens 30 and a beam splitter 32 to the proximal end of the optical fiber in laser catheter 10. When the laser catheter 10 includes more than one optical fiber, the laser beam 22 may be focused by lens 30 on the proximal ends of all the optical fibers or on the proximal ends of selected optical fibers. The diagnostic laser 20 preferably generates laser radiation in the ultraviolet wavelength range of 280–400 nanometers. In a preferred embodiment, the diagnostic laser 20 is a helium cadmium laser, which operates at 325 nanometers. The required intensity at the treatment region is on the order of 200–500 microjoules/mm$^2$. The wavelength and intensity of the diagnostic laser 20 are selected to stimulate fluorescence from tissue in the treatment region.

A portion of the fluorescence emitted by tissue in the treatment region is transmitted through the optical fiber in laser catheter 10 and is reflected by beam splitter 32 to a fluorescence analysis system. The fluorescence, indicated by reference numeral 40, passes through a lens 42, a transmission optical fiber 44 and a lens 46 to a beam splitter 50. A first portion of the fluorescence 40 passes through beam splitter 50 and an optical filter 52 to a photomultiplier 54. A second portion of the fluorescence 40 is reflected by beam splitter 50 through an optical filter 56 to a photomultiplier 58. The optical filters 52 and 56 each have a narrow bandpass characteristic for selecting a desired wavelength from fluorescence 40. Preferably, the optical filters 52 and 56 have bandwidths on the order of 10 nanometers. In a preferred embodiment as described below, the optical filter 52 is centered at a wavelength of 380 nanometers, and the optical filter 56 is centered at a wavelength of 440 nanometers. The photomultipliers 54 and 58 detect the fluorescence intensity within the band of the respective optical filters and provide electrical signals to an analog-to-digital converter 60. The analog-to-digital converter 60 converts the fluorescence intensity signals to digital values which are supplied to a microcomputer 64.

The microcomputer 64 analyzes the fluorescence intensities in accordance with predetermined criteria, as described in detail below, and provides information for controlling the laser angioplasty procedure. In general, the fluorescence spectrum is analyzed to distinguish between normal tissue and atherosclerotic tissue, as is known in the art. In addition, the fluorescence intensity at one or more wavelengths is monitored to provide additional control information, as described below.

The microcomputer 64 also controls operation of an ablation laser 70 and the shutter 24. The control may be automatic or manual. Under automatic control, the ablation laser 70 is automatically activated by the microcomputer 64 to deliver laser energy when the fluorescence 40 meets one or more predetermined criteria. Under manual control, the results of the fluorescence analysis are presented to the cardiologist, for example, on a display screen of the microcomputer 64. Then, the ablation laser 70 is activated to deliver laser energy at the option of the cardiologist. The shutter 24 is typically opened to initiate a fluorescence analysis cycle. In a preferred embodiment, the ablation laser 70 is a xenon chloride Excimer laser having an output at 308 nanometers.

It is known that laser induced fluorescence spectroscopy can be utilized to distinguish between normal tissue and atherosclerotic tissue. The results of the spectroscopic analysis are used to control the ablation laser 70. However, the fluorescence intensity is affected significantly by the presence of blood in the treatment region. The relative fluorescence intensity as a function of optical fiber tip to tissue distance in the presence of blood is plotted in FIG. 2. The fluorescence intensity is measured as the sum of intensities at 380 nanometers and 440 nanometers. The tissue fluorescence intensity decreases significantly when the fiber tip to tissue distance exceeds about 100 microns. Thus, a relatively high fluorescence intensity indicates that a fiber tip to tissue distance less than 100 microns has been achieved. The reduction in fluorescence intensity with increasing fiber tip to tissue distance is catheter dependent and, in particular, depends on the number and size of the optical fibers in the catheter. In order to achieve the goal of minimizing ablation of blood and maximizing the efficiency of tissue ablation, it is necessary to insure that the optical fiber tip is as close as possible to the tissue or to displace the blood in the region with a fluid that is substantially transparent to the wavelengths of interest.

Figure 3A:
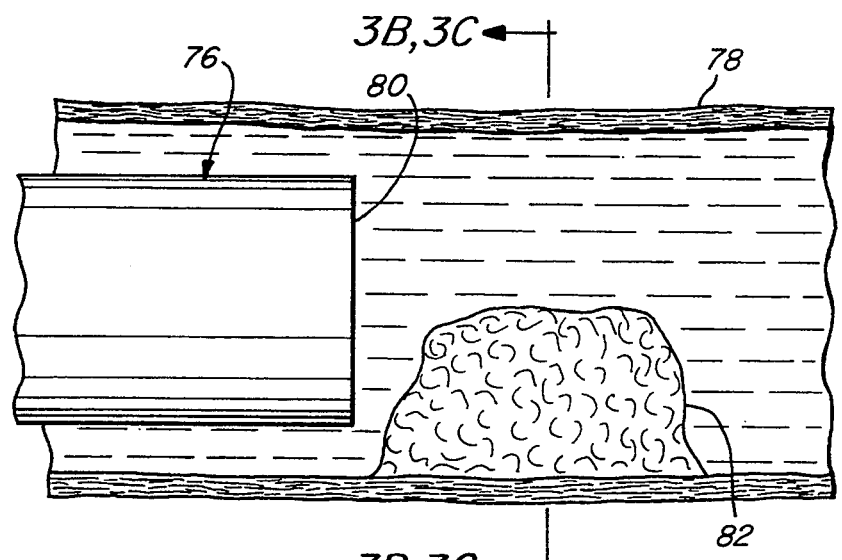
FIG. 3A is a partial cross-sectional view of a blood vessel, showing the distal end of an eccentric laser catheter positioned adjacent to a partial obstruction.
Figure 3B:
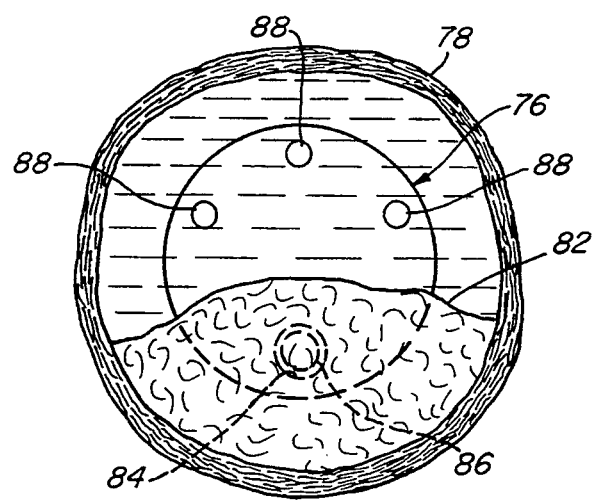
FIG. 3B is a cross-sectional view of the blood vessel and eccentric laser catheter, taken along line 3B—3B of FIG. 3A and showing the optical fibers misaligned with the obstruction.
Figure 3C:
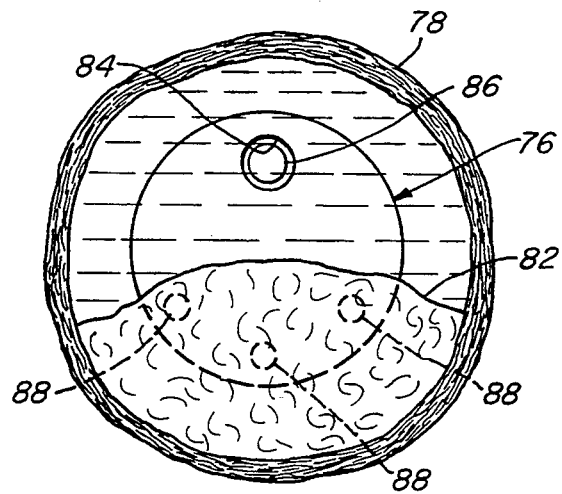
FIG. 3C is a cross-sectional view of the blood vessel and eccentric laser catheter, showing the optical fibers in alignment with the obstruction.

A method for positioning an eccentric laser catheter in accordance with a first aspect of the invention is illustrated in FIGS. 3A–3C. An eccentric laser catheter 76 is positioned in a stenosed region of a blood vessel 78 with its distal end 80 adjacent to an obstruction 82. As shown in FIGS. 3B and 3C, the catheter 76 includes a lumen 84 for a guidewire 86, which is offset from the central axis of catheter 76. The catheter 76 also includes one or more optical fibers 88. The catheter in FIGS. 3B and 3C is shown with three optical fibers 88.

The obstruction 82 of atherosclerotic tissue in the example of FIGS. 3A–3C is located on one side of the blood vessel 78. Depending on the orientation of the catheter 76 in the blood vessel 78, the optical fibers 88 may or may not be aligned with the obstruction 82. In the orientation illustrated in FIG. 3B, optical fibers 88 are misaligned with obstruction 82, and any attempt at laser induced fluorescence spectroscopy or laser ablation would fail. In FIG. 3C, the catheter 76 has been rotated so that optical fibers 88 are aligned with obstruction 82, thus permitting fluorescence spectroscopy and ablation of obstruction 82.

In order to insure that the eccentric laser catheter 76 is oriented as shown in FIG. 3C, the fluorescence intensity is monitored during positioning of the laser catheter 76. The catheter is first advanced through the blood vessel to a location as near as possible to the obstruction. Then, laser radiation from diagnostic laser 20 is transmitted through the optical fibers 88, and the fluorescence intensity is monitored. As can be seen from FIG. 2, the fluorescence intensity is low when the optical fibers 88 are misaligned with obstruction 82, because the laser radiation is directed through blood. By contrast, when the optical fibers 88 are aligned with the obstruction 82 as shown in FIG. 3C, the fluorescence intensity is relatively high.

In order to insure the optimum alignment, the laser catheter 86 is rotated about its longitudinal axis, and the fluorescence intensity is monitored. As the amount of overlap between the optical fibers 88 and the obstruction 82 increases, the fluorescence intensity increases. The optimum alignment is indicated by a maximum fluorescence intensity. In some cases, the spacing between the laser catheter 76 and the obstruction 82 may exceed the spacing required for fluorescence spectroscopy in blood (about 100 micrometers.) In these cases, the maximum fluorescence intensity during rotation of laser catheter 76 is relatively low, and it is necessary to reposition the catheter closer to the obstruction 82 prior to energizing the ablation laser. Thus, in a preferred embodiment, the catheter is rotated until maximum fluorescence intensity is indicated. The maximum intensity must exceed a predetermined threshold level which indicates that the distal end of the catheter is within the required spacing from the obstruction 82.

The obstruction 82 is shown in FIGS. 3A–3C as located on one side of the blood vessel. In general, however, the technique described above for orienting an eccentric laser catheter can be applied to any obstruction that is nonuniform around the periphery of the blood vessel. The catheter is simply rotated until a maximum fluorescence intensity is obtained, thereby indicating maximum overlap between the optical fibers and the obstruction. Furthermore, the technique can be used after tissue ablation to reposition the laser catheter for maximum overlap between the optical fibers and the obstruction to be removed.

The technique described above in connection with FIGS. 3A–3C involves rotation of an eccentric laser catheter with respect to an obstruction that is nonuniform around the periphery of the blood vessel. In an alternative approach, the distal ends of one or more optical fibers in a laser catheter or the distal end of the laser catheter itself can be deflected laterally or radially with respect to the longitudinal axis of the blood vessel to increase overlap between the optical fibers and the obstruction. Lateral or radial deflection of optical fibers in a laser catheter can be effected with wires or inflatable balloons, as is known in the art. Thus, for example, by deflecting the distal ends of optical fibers 88 downwardly in FIG. 3B, overlap between the optical fibers 88 and the obstruction 82 can be achieved. The fluorescence intensity is monitored as the optical fibers are deflected, until a maximum fluorescence intensity is observed, thereby indicating maximum overlap between the optical fibers and the obstruction. Lateral or radial deflection of the distal ends of optical fibers or of the distal end of a laser catheter and monitoring of fluorescence intensity to achieve overlap between optical fibers and an obstruction can be utilized with any laser catheter, either eccentric or concentric, with respect to any obstruction that is nonuniform around the periphery of the blood vessel.

Figure 4A:
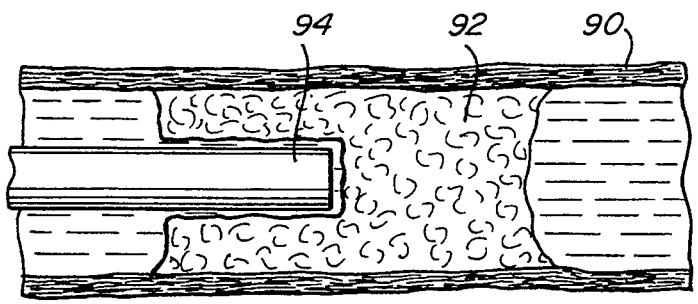
FIG. 4A is a partial cross-sectional view of a blood vessel having a total occlusion, showing a laser ablation device after partial ablation of the occlusion.
Figure 4B:
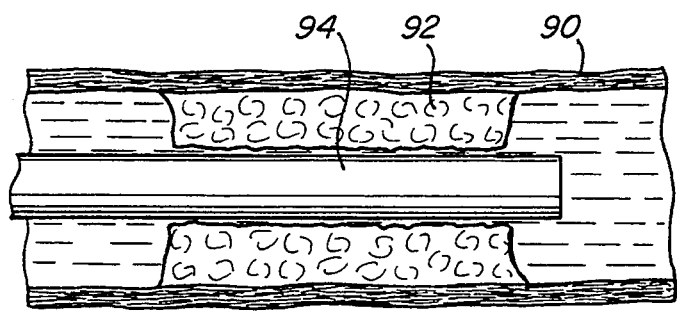
FIG. 4B is a partial cross-sectional view of the blood vessel shown in FIG. 4A after the laser ablation device has crossed the occlusion.

Another aspect of the invention is illustrated in FIGS. 4A and 4B. A blood vessel 90 is fully obstructed by an occlusion 92. A laser ablation device 94 is used to tunnel through the occlusion 92 and open a passage therethrough. The laser ablation device 94 can be any device, such as an optical fiber, a guidewire having an optical fiber, or a laser catheter, that is capable of transmitting laser radiation to the occlusion 92 and forming a passage through the occlusion. In one example, the laser ablation device 94 is a small diameter guidewire having an optical fiber that is used in conjunction with a laser catheter (not shown.) The device 94 can be centered in the blood vessel 90 by an inflatable balloon (not shown.) The passage through the occlusion 92 is preferably formed by alternating fluorescence spectroscopy and ablation in a progressive ablation procedure.

During progressive ablation through the occlusion 92, both the fluorescence spectrum and the fluorescence intensity are monitored. The fluorescence spectrum indicates the presence of atherosclerotic tissue. When the ablation is partially complete, as shown in FIG. 4A, the fluorescence intensity is relatively high, because the tissue in the occlusion 92 is directly adjacent to, and typically in contact with, the distal end of the laser ablation device 94. When the laser ablation device 94 crosses the occlusion 92, as shown in FIG. 4B, its distal end comes in contact with blood, and the fluorescence intensity drops abruptly. This drop in fluorescence intensity is used as an indication that the occlusion 92 has been crossed and that the ablation procedure can be discontinued.

Figure 5:
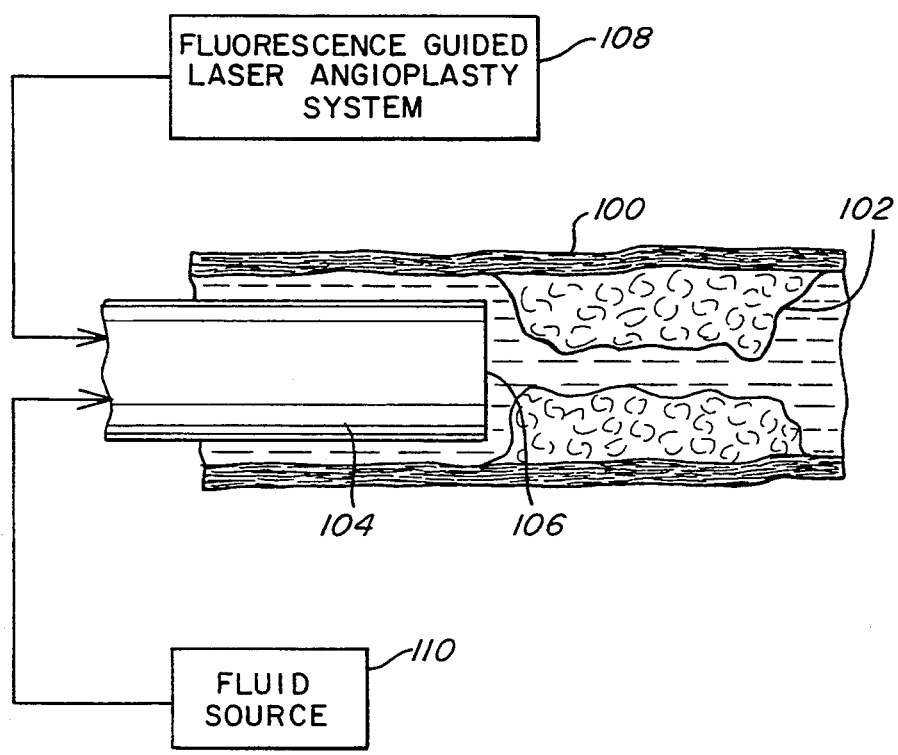
FIG. 5 is a schematic diagram that illustrates use of laser induced fluorescence intensity feedback to determine the effectiveness of fluid flushing in a blood vessel.

A further aspect of the invention is described with reference to FIGS. 5, 6A and 6B. As indicated above, the requirement for a very small fiber-to-tissue spacing in the presence of blood can be relaxed by flushing the treatment region with a transparent fluid, such as saline. A blood vessel 100 having an obstruction 102 is shown in FIG. 5. A laser catheter 104 is positioned in the blood vessel 100 with its distal end 106 adjacent to the obstruction 102. The catheter 104 includes at least one optical fiber and is connected to a fluorescence guided laser angioplasty system 108. The system 108 can be the same as the system shown in FIG. 1 and described above. The catheter 104 may include a lumen for carrying a flushing fluid from a fluid source 110 to the treatment region at the distal end of catheter 104. In another embodiment, the flushing fluid is delivered through a coaxial guide catheter that is located proximal to the laser catheter 104. Alternatively, a secondary catheter can be used for delivering the flushing fluid. In general, any desired technique for introducing a flushing fluid into the treatment region can be utilized. Typically the fluid source 110 causes a fluid, such as saline, to flow to the treatment region at predetermined, adjustable rate.

The laser catheter 104 is advanced through blood vessel 100 to the region of obstruction 102. The distal end 106 of catheter 104 is positioned in close proximity to obstruction 102. Then, a flushing fluid, such as saline, is introduced into the region of obstruction 102 from the fluid source 110. Laser radiation from the diagnostic laser 20 (FIG. 1) is transmitted through the optical fiber in catheter 104 for stimulating fluorescence. The intensity of the fluorescence is monitored in order to determine the effectiveness of fluid flushing.

Figure 6A:
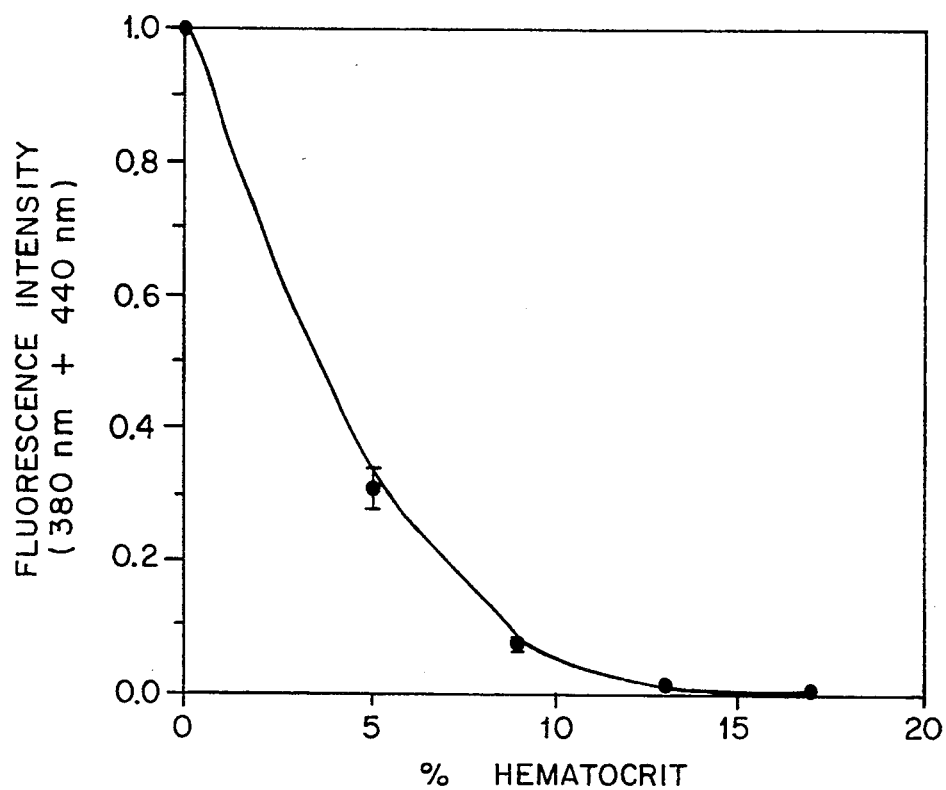
FIG. 6A is graph of relative fluorescence intensity in blood as a function of percent hematocrit.
Figure 6B:
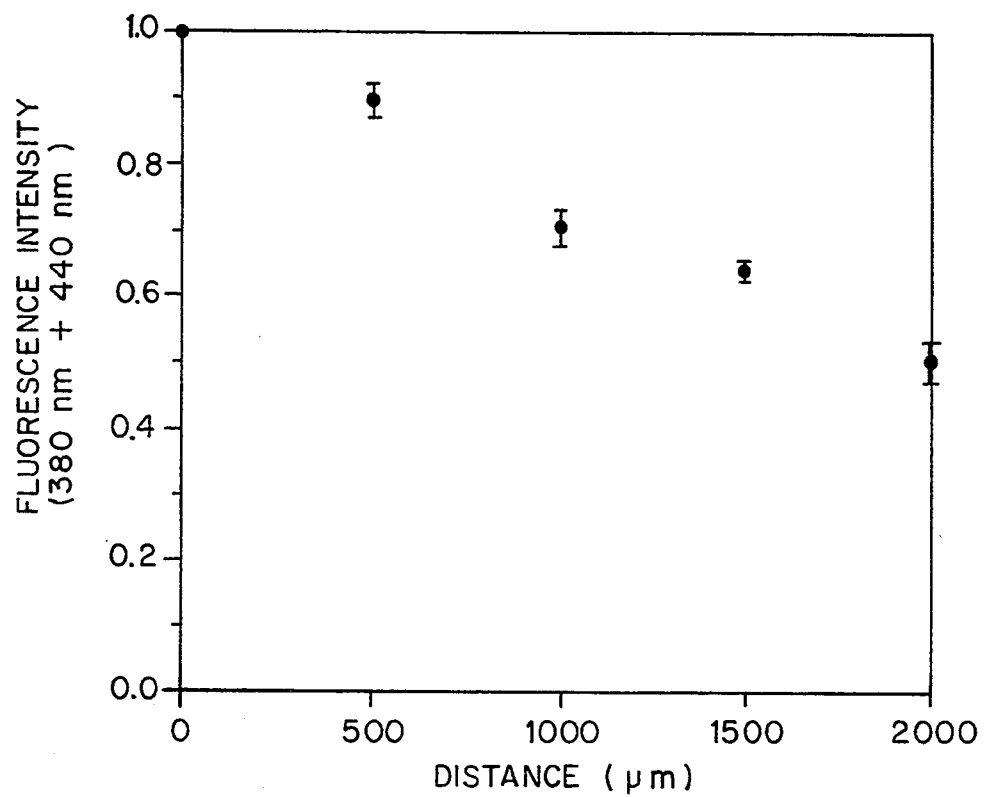
FIG. 6B is a graph of relative fluorescence intensity in saline as a function of distance between the distal end of the optical fiber and tissue.

The relative fluorescence intensity in blood is plotted in FIG. 6A as a function of percent hematocrit for a catheter-to-tissue spacing of 300 micrometers. It can been seen that the saline must dilute the blood to less than about 5% hematocrit in order to obtain sufficient fluorescence intensity for spectroscopic analysis. The relative fluorescence intensity in saline is plotted as a function of distance between the optical fiber tip and the tissue in FIG. 6B. The fluorescence intensity remains relatively high, even for fiber-to-tissue spacings of up to 2,000 micrometers. In FIGS. 6A and 6B the fluorescence intensity is measured as the sum of intensities at 380 nanometers and 440 nanometers.

The effectiveness of saline flushing is determined by measuring the fluorescence intensity after introduction of flushing fluid. A high fluorescence intensity indicates effective flushing in the treatment region, whereas a low fluorescence intensity indicates that blood remains in the treatment region. For example, when dilution of the blood to less than 5% hematocrit is desired, a relative fluorescence intensity of about 0.4 or greater must be observed, as shown in FIG. 6A. When the fluorescence intensity is less than the value which corresponds to the desired blood dilution, the amount of flushing fluid in the treatment region is increased, for example, by increasing the rate of fluid flow to the treatment region, or by introducing an additional quantity of fluid into the treatment region. When effective dilution has been achieved, laser-induced fluorescence spectroscopy and tissue ablation can be performed as described above.

Figure 7:
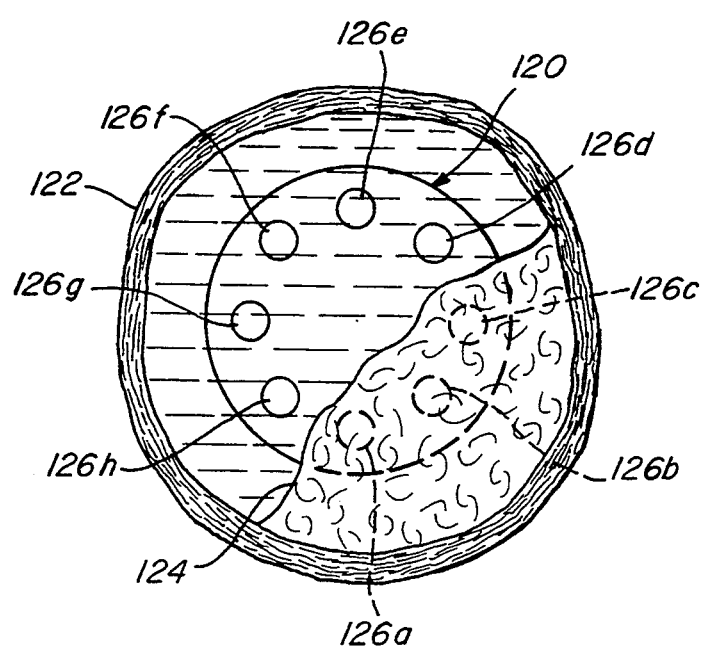
FIG. 7 is a cross-sectional view of a blood vessel having a laser catheter positioned therein, showing a partial obstruction located adjacent to group of optical fibers in the catheter.

Yet anothertaspect of the present invention is described with reference to FIG. 7. A laser catheter 120 is positioned in a blood vessel 122 adjacent to an obstruction 124. The laser catheter 120 includes a plurality of optical fibers 126a–126h. Optical fibers 126a–126c are aligned with obstruction 124, whereas optical fibers 126d–126h are not aligned with obstruction 124.

Subsets of optical fibers are defined within laser catheter 120 to permit fluorescence analysis and ablation for each subset. In the present example, each subset includes one optical fiber. However, it will be understood that each subset can include one or more optical fibers. Preferably, the optical fibers in a subset are located in close proximity to each other within the laser catheter 120. The fluorescence guided laser angioplasty system shown in FIG. 1 and described above is optically coupled to the optical fibers 126a–126h such that the laser energy from diagnostic laser 20 and ablation laser 70 can be individually directed to each subset of optical fibers.

Figure 2:
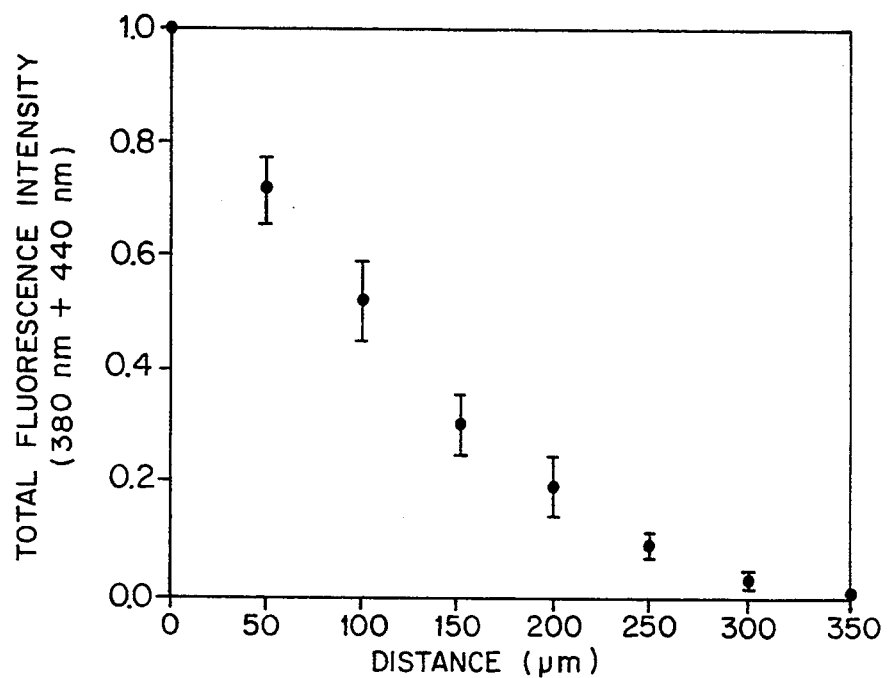
FIG. 2 is a graph of relative fluorescence intensity as a function of fiber-to-tissue distance in the presence of blood.

In an example of sequential fluorescence analysis and ablation, low power ultraviolet laser radiation from diagnostic laser 20 is directed through optical fiber 126a, and the fluorescence is analyzed. In particular, the fluorescence spectrum is analyzed to distinguish between normal tissue and atherosclerotic tissue, and the fluorescence intensity is monitored to determine whether the distal end of optical fiber 126 is within a desired distance of obstruction 124. The fluorescence intensity varies as a function of fiber-to-tissue distance, as shown in FIG. 2. When the fluorescence spectral analysis indicates the presence of atherosclerotic tissue and the fluorescence intensity indicates that the optical fiber 126a is within a desired spacing from obstruction 124, the ablation laser 70 is activated to deliver laser energy, thereby causing a portion of the obstruction 124 adjacent to optical fiber 126a to be ablated. This procedure is repeated for each of the optical fibers in laser catheter 120. For optical fibers 126d–126h, the fluorescence analysis does not meet the criteria described above, and the ablation laser 70 is not activated to deliver laser energy. For optical fibers 126b and 126c, the criteria are met and the obstruction 124 is ablated. Even for fibers 126a–126c that are aligned with the obstruction 124, the fiber-to-tissue spacing may exceed the predetermined maximum value, as indicated by a low fluorescence intensity, and the ablation laser 70 may not be activated to deliver laser energy. The process of fluorescence analysis and ablation is repeated for each optical fiber in the catheter, thus permitting precise control over diagnosis of atherosclerotic tissue, optical fiber positioning and tissue ablation.

In accordance with the present invention, fluorescence intensity feedback is used to control laser angioplasty. The fluorescence intensity can be measured at one or more specific wavelengths, or can be measured over a broad band (such as 350–600 nanometers.) In a preferred embodiment, the fluorescence intensity is evaluated as the sum of intensities at two wavelengths, preferably the wavelengths used for spectral analysis. In a preferred fluorescence spectral analysis, the ratio of fluorescence intensities at wavelengths of 380 nanometers and 440 nanometers is determined. The fluorescence intensity is calculated as the sum of intensities at 380 and 440 nanometers. This approach has the advantage that the same optical elements are used for spectral analysis and for determining fluorescence intensity. In another embodiment, the fluorescence intensity is determined at a single wavelength, such as 380 nanometers. It will be understood that the fluorescence intensity can be evaluated at one or more wavelengths different from those used for spectral analysis.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A method for controlling the effectiveness of fluid flushing in a blood vessel, comprising the steps of:

advancing a catheter through a blood vessel to a region of interest, said catheter including an optical fiber extending therethrough;

introducing a flushing fluid into the region of interest in the blood vessel;

stimulating fluorescence from material in the region of interest adjacent to the distal end of said optical fiber by transmitting through said optical fiber laser radiation having a wavelength and intensity to stimulate such fluorescence;

monitoring the intensity of the fluorescence from material in the region of interest; and increasing the amount of flushing fluid in the region of interest if the intensity of said fluorescence is representative of less than a desired amount of flushing fluid in the region of interest.

2. A method as defined in claim 1 wherein the step of increasing the amount of flushing fluid is performed until the fluorescence intensity exceeds a predetermined value representative of the desired amount of flushing fluid in the region of interest.

3. A method as defined in claim 2 wherein the step of monitoring the fluorescence intensity includes monitoring the sum of fluorescence intensities at two or more wavelengths.

4. A method as defined in claim 3 wherein the step of monitoring the sum of fluorescence intensities includes monitoring the sum of fluorescence intensities at 380 nanometers and 440 nanometers.

5. A method as defined in claim 2 wherein the step of monitoring the fluorescence intensity includes monitoring the fluorescence intensity near a single wavelength.

6. A method as defined in claim 5 wherein the step of monitoring the fluorescence intensity near a single wavelength is performed near 380 nanometers.

7. A method as defined in claim 1 wherein the step of increasing the amount of flushing fluid includes increasing a rate of fluid flow to the region of interest.

8. A method as defined in claim 1 wherein the step of increasing the amount of flushing fluid includes introducing additional fluid into the region of interest.

9. A method as defined in claim 1 wherein said flushing fluid is substantially transparent to the fluorescence wavelengths of interest.

10. A method as defined in claim 1 wherein said flushing fluid comprises saline.

11. A method as defined in claim 1 wherein the step of stimulating fluorescence includes transmitting laser radiation in a wavelength range of 280 to 400 nanometers.

* * * * *